United States Patent
Adachi et al.

(10) Patent No.: US 9,472,319 B1
(45) Date of Patent: Oct. 18, 2016

(54) COMPOSITE CABLE

(71) Applicant: Junkosha Inc., Kasama-shi (JP)

(72) Inventors: Tomohiro Adachi, Kasama (JP); Shunsuke Munakata, Kasama (JP)

(73) Assignee: Junkosha Inc., Kasama-Shi (JP)

( * ) Notice: Subject to any disclaimer, the term of this patent is extended or adjusted under 35 U.S.C. 154(b) by 0 days.

(21) Appl. No.: 15/038,138

(22) PCT Filed: Dec. 3, 2014

(86) PCT No.: PCT/JP2014/082006
§ 371 (c)(1),
(2) Date: Jul. 11, 2016

(87) PCT Pub. No.: WO2015/076426
PCT Pub. Date: May 28, 2015

(30) Foreign Application Priority Data

Nov. 20, 2013 (JP) ................. 2013-240488

(51) Int. Cl.
| H01B 3/30 | (2006.01) |
| H01B 7/04 | (2006.01) |
| H01B 9/00 | (2006.01) |
| H01B 7/42 | (2006.01) |
| H02G 3/04 | (2006.01) |
| B29K 27/18 | (2006.01) |
| H01B 11/02 | (2006.01) |

(52) U.S. Cl.
CPC ................ *H01B 7/04* (2013.01); *H01B 7/425* (2013.01); *H01B 9/005* (2013.01); *H02G 3/0437* (2013.01); *B29K 2027/18* (2013.01); *H01B 11/02* (2013.01); *H05K 2201/0116* (2013.01)

(58) Field of Classification Search
CPC ........ H01B 11/02; H01B 7/04; H01B 9/005; H01B 7/425; H02G 3/0437; B29K 2027/18; H05K 2201/0116
USPC ..... 174/110 PM, 110 R, 113 R, 137 R, 99 R, 174/68.1
See application file for complete search history.

(56) References Cited

U.S. PATENT DOCUMENTS

| 5,574,250 A | 11/1996 | Hardie et al. |
| 6,025,044 A * | 2/2000 | Campbell ............... A61L 27/16 428/35.8 |
| 2008/0302556 A1* | 12/2008 | Varkey ................... H01B 7/292 174/120 R |
| 2012/0295144 A1* | 11/2012 | Kwon ................... H01M 4/134 429/94 |

FOREIGN PATENT DOCUMENTS

| JP | 9511359 A | 11/1997 |
| JP | 2002515632 A | 5/2002 |
| JP | 20129156 A | 1/2012 |
| WO | 9959162 A1 | 11/1999 |

* cited by examiner

*Primary Examiner* — James Wu
(74) *Attorney, Agent, or Firm* — The Webb Law Firm

(57) ABSTRACT

A composite cable having, on the inside of a sheath, a tube and a plurality of cables. When said composite cable is suspended in a hoop shape with the entire composite cable as a cable to be tested, if the maximum value for the inner diameter of said hoop is measured as D1 and the inner diameter of the hoop at a position 100 mm from the top edge of the hoop when the hoop is subjected to a load of 1 kg is measured as D2, the condition D1−D2>70 mm is satisfied. The tube partially or entirely includes a layer made from porous polytetrafluoroethylene, and if the outer diameter and the inner diameter of the layer of the tube are respectively defined as (D) and (d), the condition (D−d)/D falls within the range of 0.27 to 0.75.

1 Claim, 6 Drawing Sheets

AWG36 shielded twisted-pair cable

AWG38 simple line seven-core cable units

AWG40 50pF coaxial twelve-core cable unit about 60 m weight 1 kg

COMPOSITE CABLE

CROSS-REFERENCE TO RELATED APPLICATIONS

This application is the United States national phase of International Application No. PCT/JP2014/082006 filed Dec. 3, 2014, and claims priority to Japanese Patent Application No. 2013-240488 filed Nov. 20, 2013, the disclosures of which are hereby incorporated in their entirety by reference.

FIELD OF THE DISCLOSURE

The present disclosure relates to a composite cable, especially, to a composite cable having, on the inside of a sheath, a tube and a plurality of cables such as signal lines and power supply lines.

DESCRIPTION OF THE RELATED ART

Typically, in a field of a medical device or the like, a composite cable having a tube, into which an optical fiber is fitted or fluid for cooling is recirculated, and a plurality of cables such as signal lines and power supply lines on the inside of a sheath of the cable has been used. As an example of this typical composite cable, in Patent Document 1, disclosed is a composite cable having an optical fiber and a plurality of wires on the inside of a sheath, in which the optical fiber is accommodated in a protective tube of a predetermined hardness and the plurality of wires are disposed around the protective tube.

RELATED ART DOCUMENT

Patent Document

Patent Document 1: Japanese Patent Application Laid-Open Publication No. 2012-9156

SUMMARY OF THE DISCLOSURE

Technical Problem to be Solved

In such a typical composite cable, generally, the inside optical fiber is protected or the fluid is recirculated by preventing the tube from being bended (deformed), so that the tube is prevented from being clogged, and especially, sealing performance (airtightness and liquid tightness) needs to be secured when the fluid is recirculated in the tube. Meanwhile, for example, when generally using the cable or the like to connect a device and a probe thereof, since the cable highly needs to be deformed pliably in response to operation of the probe, it is preferred to have high flexibility and pliability over the entire composite cable. In the composite cable disclosed in the Patent Document 1, since tetrafluoroethylene-ethylene copolymer (ETFE) having a solid structure is formed as a tube, which accommodates the optical fiber, and a protective tube having hardness of 65 or higher of resin shore D is used, it is superior to protect the internal optical fiber in order to prevent the tube from being bended, but it is difficult to obtain the flexibility and the pliability over the entire composite cable in order to include the tube having high hardness. In this regard, the tube cannot be prevented from being efficiently bended by tinning a thickness of the tube to simply obtain the flexibility, so that quality stability over the entire composite cable may be deteriorated. For this reason, a technique to improve the quality stability over the entire composite cable by improving both of the flexibility and deformation performance while keeping both is expected.

An object of the present disclosure provides the composite cable which can obtain the high quality stability by improving both of the flexibility and the deformation performance.

SUMMARY OF THE INVENTION

As a result that the present inventor has closely studied a configuration of a composite cable, in which quality stability and flexibility over the entire composite cable are balanced, the inventor noticed a microscopic (electron-microscopic) structure of an inner portion of the composite cable, found that it is difficult to obtain pliability and the flexibility over the entire composite cable when the composite cable has a solid type tube structure, and it is noticed that the pliability and the flexibility over the entire composite cable can be obtained when the structure of the tube is a porous structure but bending characteristics of the tube may be deteriorated, and as a result that the inventor has closely further studied structures (material quality, test characteristic, thickness, porous shape, multilayer structure) of the tube or a relation (outer diameter of inner conductor of signal line) between signal lines around the tube, the structure of the composite cable, in which the quality stability over the entire composite cable is secured and the flexibility obtained, was found.

That is, to achieve the purpose, the composite cable of the present disclosure is a composite cable which has, on the inside of a sheath, a tube and a plurality of cables, and when the composite cable is suspended in a hoop shape with the entire composite cable as a cable to be tested, if a maximum value for an inner diameter width of the hoop is measured as D1 and the inner diameter width of the hoop at a position 100 mm from a top edge of the hoop when the hoop is subjected to a load of 1 kg is measured as D2, a condition D1−D2>70 mm is satisfied, and further the tube partially or entirely comprises a layer made from porous polytetrafluoroethylene (hereinafter, may be abbreviated to ePTFE), and if an outer diameter and an inner diameter of the layer of the tube are respectively defined as (D) and (d), a condition (D−d)/D falls within a range of 0.27 to 0.75, and has a predetermined porous structure inside a region obtained by joining the following four points: two points at which an average crevasse width of the porous structure in ePTFE has a minimum value of 10.0 μm and a maximum value of 20.0 μm when a ratio (D−d)/D is 0.27, and two points at which the minimum value is 16.0 μm and the maximum value is 27.0 μm when the ratio (D−d)/D is 0.75.

With the configuration, since the tube is partially or entirely made from the ePTFE, the flexibility and the pliability are improved as compared to, for example, the typical composite cable using the tube of the solid structure. Further, if the outer diameter and the inner diameter of the tube are respectively defined as (D) and (d), the condition (D−d)/D falls within the range of 0.27 to 0.75 and has the predetermined porous structure inside the region obtained by joining the following four points: the two points at which the average crevasse width of the porous structure in the ePTFE has the minimum value of 10.0 μm and the maximum value of 20.0 μm when the ratio (D−d)/D is 0.27, and the two points at which the minimum value of 16.0 μm and the maximum value of 27.0 μm when the ratio (D−d)/D is 0.75, so that fine deformation resistance performance can be obtained. Here, although the tube is partially or entirely made from the porous polytetrafluoroethylene (ePTFE), the porous structure is not a focused concept to a void ratio in a void content of the porous structure but a focused concept to the porous crevasse width as described above.

That is, the inventor's knowledge, the tube is made from the ePTFE, and if the outer diameter and the inner diameter of the tube are respectively defined as (D) and (d), the condition (D−d)/D falls within the range of 0.27 to 0.75 and has the structure inside the region obtained by joining the following four points: the two points at which the average crevasse width of the porous structure has the minimum value of 10.0 μm and the maximum value of 20.0 μm when the ratio (D−d)/D is 0.27, and the two points at which the minimum value is 16.0 μm and the maximum value is 27.0 μm when the ratio (D−d)/D is 0.75, so that the flexibility and the pliability and the performance of the tube are balanced. Further, in the composite cable, when the composite cable is suspended in the hoop shape with the entire composite cable as the cable to be tested, if the maximum value for the inner diameter width of the hoop is measured as D1 and the inner diameter width of the hoop at the position apart from the top edge of the hoop by 100 mm when the hoop is subjected to the load of 1 kg is measured as D2, the condition D1−D2>70 mm is satisfied, and therefore, the flexibility and the pliability over the entire composite cable can be secured.

DETAILED DESCRIPTION OF THE PREFERRED EMBODIMENTS

Figure 1:
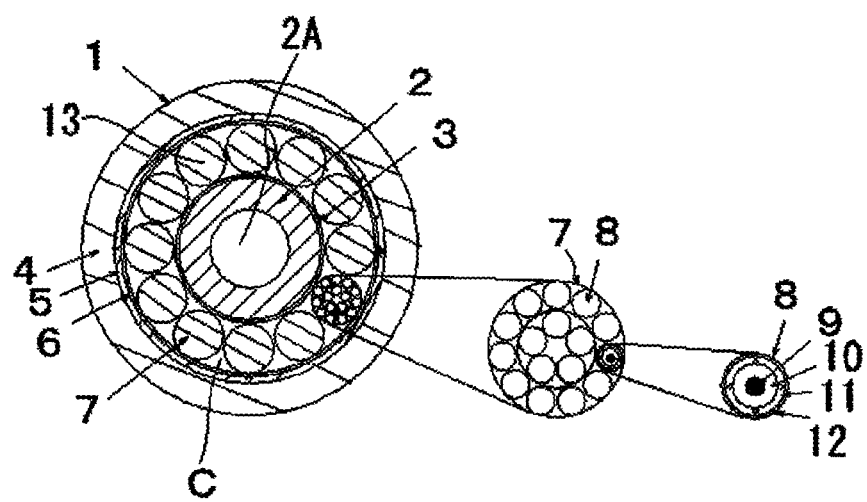
FIG. 1 is a partially enlarged cross-sectional view of a composite cable in the first exemplary embodiment of the present disclosure.

The embodiment explained in detail below relates to but is not limited to the disclosure described in the claims, and it should also be noted that all combinations of the features described in the present embodiment are not necessarily essential to the establishment of the present disclosure. FIG. 1 is a partially enlarged cross-sectional view of a composite cable in the first exemplary embodiment of the present disclosure. As illustrated in FIG. 1, a composite cable 1 in the present disclosure has a tube 2 disposed in a center of a cross section of the composite cable 1 and a plurality of cable units 7 disposed around the tube 2. The tube 2 has a cavity 2A, into which a non-illustrated optical fiber or the like is inserted. A tape 3 is wound on an outer circumferential surface of the tube 2, and an outer side of the tape 3 is referred to as a cable accommodation portion C. In the cable accommodation portion C, the plurality of cable units 7 and interpositions 13 are disposed throughout an outer circumference of the tape 3 to be twisted each other. A press winding tape 6 press winds an outer side of the twisted cable units 7 or the like, an outer side of the press winding tape 6 is shielded by a collective shield layer 5, and a cable sheath 4, which is an outermost layer, is disposed on an outer side of the collective shield layer 5. Further, a thickness of the cable accommodation portion C (a distance between an outer circumference of the tape 3 and an inner circumference of the press winding tape 6) is desirably identical to or slightly larger than outer diameters of the cable units 7 and the interpositions 13. Each cable unit 7 is, for example, a twisted pair cable, a coaxial cable insulating cable or the like having AWG 38 to 55 under AWG (American Wire Gauge). Further, each cable unit 7 is a unit in which a plurality of wires are disposed on an inner side and a plurality of signal lines 8 or the like are disposed on an outer side thereof, and each signal line 8 is an extremely fine coaxial cable or the like in which an inner conductor 9 formed from tin plated annealed copper wires and copper alloy wires is disposed in a center, a dielectric material 10 is interposed around the inner conductor, an outer conductor 11 is disposed coaxially with the inner conductor 9, and a circumferential surface thereof is coated by an insulating coating 12. An outer diameter of the inner conductor 9 is preferred to be 0.123 mm or less. That is, in the inventor's knowledge, a hardness over the entire composite cable depends on a hardness of the inner conductor such as signal lines around the tube or the like as well as a hardness of the tube, and by increasing the outer diameter of the inner conductor 9, the inner conductor 9 becomes harder, so that it is possible to further improve flexibility and pliability over the entire composite cable by setting the outer diameter of the inner conductor 9 to be 0.123 mm or less.

Further, other structures, that is, detail of the press winding tape 6, the collective shield layer 5 and the cable sheath 4, also, the number of cables (units) 7 or a structure of each cable unit 7 may not be problems as long as the composite cable of the present disclosure has the tube 2 and the plurality of cables (units) 7. Furthermore, the cable units 7 may not be twisted.

The tube 2, which constitutes a big characteristic of the composite cable 1, is made from porous polytetrafluoroethylene (ePTFE), and if an outer diameter and an inner diameter of the tube 2 are respectively defined as (D) and (d), a condition (D−d)/D falls within a range of 0.27 to 0.75. Further, the condition (D−d)/D has a predetermined porous structure inside a region obtained by joining the following four points: two points at which a crevasse width of a porous structure in an ePTFE, layer of the tube 2 has a minimum value of 10.0 μm and a maximum value of 20.0 μm when a ratio (D−d)/D is 0.27, and two points at which a minimum value is 16.0 μm and a maximum value is 27.0 μm when the ratio (D−d)/D is 0.75.

The signal line 8 has, for example, a conductor having an outer diameter of 0.30 mm, in which seven element wires of a thin diameter formed of the tin plated annealed copper wires and the copper alloy wires are twisted. Then, by covering this conductor with a sheath having an insulating thickness of 0.14 mm, a wire 15 having an outer diameter of 0.58 mm is formed. Further, a wire 15, which is an electric power line, has, for example, a conductor of an outer diameter of 0.38 mm, in which seven element wires with an outer diameter of 0.127 mm and formed of the tin plated annealed copper wires and the copper alloy wires are twisted. Then, by covering this conductor with a sheath having an insulating thickness of 0.1 mm, the wire 15 having the outer diameter of 0.58 mm is formed. The signal line and the electric power line are divided into two. As a material of the insulating coating 12, for example, tetrafluoroethylene/perfluoroalkyl (vinyl ether) copolymer (PFA) having high heat resistance, chemical resistance, nonadherent, self-lubricating or the like may be used. As the press winding tape 6, for example, a resin tape which is formed from polyethylene terephthalate (PET) resin having high heat resistance, wear resistance or the like may be used, but a paper tape or a resin tape of polytetrafluoroethylene (PTFE) resin or the like may be used. The collective shield layer 5, for example, is formed by braiding the tin plated copper alloy wires having an outer diameter of several tens μm, but may be formed by cross-winding the copper alloy wires or by winding the metal resin tape formed from the polyethylene terephthalate (PET) resin with a metal resin tape on which copper foil or aluminum foil is formed. The cable sheath 4, for example, is formed of polyvinyl chloride (PVC), polyolefin-based resin or the like. The cable sheath 4, for example, has a thickness of about 0.25 mm and an outer diameter of 3.0 mm.

In the composite cable 1 having this configuration, since the tube 2 is made from the ePTFE, the flexibility and the pliability are improved, for example, as compared to the typical composite cable in which a tube made from only polytetrafluoroethylene (hereinafter, may be abbreviated to PTFE) having a solid structure is used. Further, if the outer diameter and the inner diameter of the tube 2 are respectively defined as (D) and (d), the condition (D−d)/D falls within the range of 0.27 to 0.75 and has the predetermined porous structure inside the region obtained by joining the following four points: the two points at which the crevasse width of the porous structure in the ePTFE has the minimum value of 10.0 μm and the maximum value of 20.0 μm when the ratio (D−d)/D is 0.27, and the two points at which the minimum value is 16.0 μm and the maximum value is 27.0 μm when the ratio (D−d)/D is 0.75, so that fine deformation resistance performance can be obtained. Here, although the tube 2 is made from the porous polytetrafluoroethylene (ePTFE), and the porous structure is, in case of the porous structure, not a focused concept on a ratio occupied by empty pores such as empty pore ratio but a focused concept on the porous crevasse width as described above. In the inventor's knowledge, the tube is made from the ePTFE and if the outer diameter and the inner diameter of the tube are respectively defined as (D) and (d), the condition (D−d)/D falls within a range of 0.27 to 0.75 and has the structure inside the region obtained by joining the following four points: the two points at which the crevasse width of the porous structure has the minimum value of 10.0 μm and the maximum value of 20.0 μm when the ratio (D−d)/D is 0.27, and the two points at which the minimum value is 16.0 μm and the maximum value is 27.0 μm when the ratio (D−d)/D is 0.75, so that the flexibility and the pliability of the tube and the deformation resistance performance of the tube may be balanced. Furthermore, in the composite cable, when the composite cable is suspended in a hoop shape with the entire composite cable as a cable to be tested, if a maximum value for an inner diameter width of the hoop is measured as D1 and the inner diameter width of the hoop at a position 100 mm from a top edge of the hoop when the hoop is subjected to a load of 1 kg is measured as D2, the condition D1−D2>70 mm is satisfied, and therefore, the flexibility and the pliability over the entire composite cable can be secured. Moreover, since the outer diameter of each inner conductor 9 is 0.123 mm or less, it is possible to suppress an excess lateral pressure and generation of excess bending or twist from the signal line 8 of the cable (unit) 7 into the tube 2.

Further, in the cavity 2A of the tube 2 in the exemplary embodiment, the non-illustrated optical fiber or the like is inserted, but not limited to the optical fiber. Furthermore, the numbers, thicknesses and kinds of the cable units 7 and the interpositions 13 are not limited to the above exemplary embodiment. According to the number of the cable units 7, the interpositions 13 may not be provided as long as a cross section of the cable sheath 4 becomes circular by disposing only the cable units 7 without providing the interpositions 13 in the cable accommodation portion C.

Figure 2:
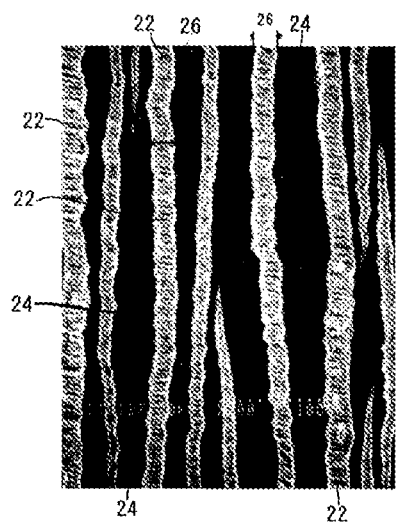
FIG. 2 is an electron micrograph of a tube of the composite cable in the first exemplary embodiment of the present disclosure, which discloses a definition of a predetermined porous structure.

FIG. 2 is an electron micrograph of the tube of the composite cable in the first exemplary embodiment of the present disclosure, and the predetermined porous structure of the tube will be explained with reference to the micrograph. The electron micrograph illustrated in FIG. 2 is the micrograph showing a cross section of the layer made from the ePTFE of the tube 2 in FIG. 1 in a longitudinal direction of the tube 2 (in other words, a micrograph showing the cross section in a backside direction of the paper in FIG. 1). In the ePTFE layer of the tube 2 of the composite cable 1 of the present exemplary embodiment, an entire resin structure illustrated in FIG. 2 is "a predetermined porous structure", a portion 22 of a gap in the resin structure is "a crevasse", and a portion 24 of a real thickness is "a node". Further, "the crevasse width" indicates a width in a horizontal direction (a transversal direction in the paper of FIG. 2, that is, an orthogonal direction to the longitudinal direction of the crevasse) in the identical drawing of the crevasse as illustrated with a reference number 26. Furthermore, "an average crevasse width" is an average value of the crevasse width 26 in the predetermined porous structure of the ePTFE layer in the tube 2. When calculating this average crevasse width, thirty any crevasses are selected, a maximum crevasse width among the respective crevasses is measured, and an average thereof is calculated.

Here, a manufacturing method of the tube 2 having the porous structure formed of the ePTFE in the composite cable of the present exemplary embodiment will be disclosed. To manufacture the tube 2 in the composite cable of the present exemplary embodiment, after firstly lumps of PTFE fine powder (product name POLYFLON PTFE F-104, from Daikin Industries) are removed through a #10 sieve and put into a poly bottle, a predetermined amount of extrusion aids (product name: CL317#2 from Yamaichi Chemical Industries) is added (refer to table below), and then the PTFE is left and aged under a transition temperature 19° or less at a room temperature for twelve hours or more. Thereafter, this is mixed in a tubular mixer for five minutes and then the mixed sample is left in the room temperature for one hour or more. Thereafter, in a paste extrusion method, the sample is put into a preliminarily molding machine while removing the lumps through the #10 sieve to obtain a tube molding body. At this time, a preliminarily molding pressure is 11.5 kg/cm². In a paste extruder (cylinder diameter 76.2 mm, mandrel diameter 18.8 mm), a mold (a die 6.85 mm chip) uses those corresponding to a desirable thickness, in the below table. Thereafter, a preliminary molding body is put in the extruder, a second preliminary molding is performed thereon under force of 14.5 kN for one minute, a ram speed is adjusted such that a predetermined press disclosed in the table below is performed, and the extruded tube molding body is wound off by a winder. Here, the press means a pressure by which the paste extruder presses the preliminarily molding body. Thereafter, the wound tube is attached to a transmitter, a drying process is performed, and the tube is wound off by the winder. Thereafter, a rotation speed of a capstan roll in a furnace of a high temperature is adjusted to a predetermined speed disclosed in the table below. Thereafter, the tube is passed at a taking-up speed disclosed in the table below in a baking furnace which is set to be at 400°, and the tube is baked. At that time, while the tube is being baked, a transmission speed is adjusted to suppress excess tension. In this way, a desirable crevasse width is adjusted by the extrusion aids, the press and the rotation speed of the capstan roll (capstan speed). Specifically, by adjusting the extrusion aids and the press, the PTFE fine powder is fiberized, so that the further uniformed crevasse may be formed. For example, if these are lacking and excess, it is difficult to form the tube, and although the crevasse can be formed, an ununiformed crevasse is formed. A relation between the extrusion aids and the press and the crevasse width will be described in Table 1 and Table 2, which will be described in detail in a subsequent section. Further, by adjusting the capstan speed, a taking-up speed of the tube is adjusted, and, accordingly, a degree of split (that is, becomes crevasse) which occurs on the tube may be adjusted. That is, the crevasse width tends to be increased by increasing the capstan speed.

TABLE 1

| | Die/chip (mm) | Extrusion aid (wt %) | Press (kN) | Capstan speed | Taking-up speed when baking | Outer diameter/inner diameter | Thickness (mm) |
|---|---|---|---|---|---|---|---|
| Exemplary embodiment 1 | 6.95/5.30 | 17 | 95 | 1.46 | 0.8 | 5.9/3.95 | 0.8 t |
| Exemplary embodiment 2 | 6.95/5.30 | 16 | 115 | 2.18 | 0.8 | 5.9/3.95 | 0.8 t |
| Exemplary embodiment 3 | 6.95/5.30 | 15 | 125 | 3.82 | 0.8 | 5.9/3.95 | 0.8 t |
| Exemplary embodiment 4 | 6.70/1.75 | 17 | 50 | 1.33 | 0.5 | 6.14/2.05 | 2.25 t |
| Exemplary embodiment 5 | 6.70/1.75 | 16 | 65 | 1.77 | 0.5 | 6.14/2.05 | 2.25 t |
| Exemplary embodiment 6 | 6.70/1.75 | 15 | 75 | 2.21 | 0.5 | 6.14/2.05 | 2.25 t |

EXEMPLARY EMBODIMENT

Respective kinds of test cables are manufactured, the flexibility of the respective composite cable and further an internal pressure and resistance R performance thereof, which serve as deformation performance, are evaluated.

(A) Composite Cable to be Evaluated

Figure 3:
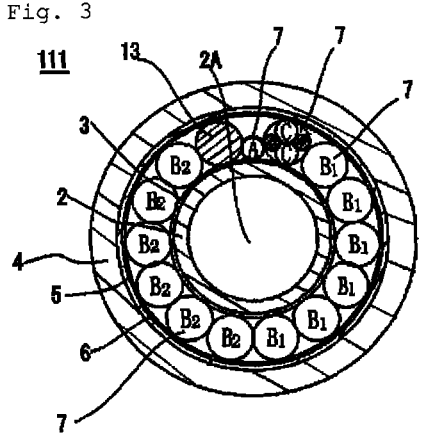
FIG. 3 is a partially enlarged cross-sectional view of a test cable in respective experiments performed on the composite cable in the first exemplary embodiment of the present disclosure.
Figure 3:
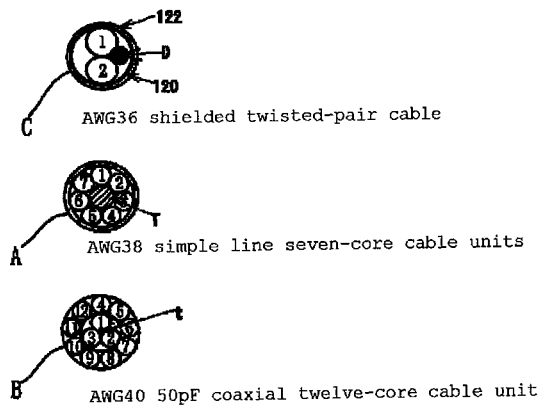

A cross section of the test cable is illustrated in FIG. 3. As illustrated in FIG. 3, a test cable 111 has a substantially identical configuration to the composite cable 1 illustrated in FIG. 1, and therefore, like reference numerals refer like parts and the description thereof will be omitted. Further, in the test cable 111, simple line seven-core cable units of AWG38 A, 50 pF coaxial twelve-core cable units of AWG40 B and shielded twisted-pair cables of AWG36 C are used in the cable unit 7 and detailed structures thereof are partially enlarged and illustrated. In the cable unit A, a tension member T having a substantially identical diameter to each core is disposed in a center, and the simple lines (cables) 1 to 7 of seven cores are disposed around the tension member, as enlarged and illustrated in the same drawing. Further, in the cable unit B, coaxial cables 1, 2 and 3 of three cores are disposed through an extremely fine tension member t in a center, and coaxial cable 4 to 12 are disposed on an outer circumference thereof. Furthermore, in the shielded twisted-pair cable C, twisted-pair cables 1 and 2 are disposed, a drain wire D is disposed on the one side, and outer sides thereof are coated by an ALPET 120 and a jacket 122. In the test cable 111 having above described structure, three kinds of evaluation tests are performed on samples (examples) 1 to 6, which are made from the ePTFE and use tubes having the porous structure manufactured in the above-described manufacturing method and conditions disclosed in Table 1, samples (comparative examples) 7 and 8, which use tubes having a solid structure and being made from FEP, and a composite cable (comparative example) 9, which uses a cable instead of the tube 2. Further, the samples (examples) 1 to 6, the samples (comparative examples) 7 and 8 have different sizes and thicknesses of respective tubes other than the material, and the sample (comparative example) 9 has the cable as a sample instead of the tube 2. These manufacturing conditions of the samples (examples) 1 to 6 are disclosed in Table 1 below, and those of the samples (comparative examples) 7, 8 and 9 are disclosed in Table 2, which will be described in detail in a subsequent section. Further, in the samples (examples) 1 to 6, the average of respective crevasse widths is disclosed in Table 2, which will be described in detail in a subsequent section. Crevasse widths at any position of the cross-sectional micrograph illustrated in FIG. 2 in the samples (examples) 1 to 6 are measured and an average value of these crevasse widths is calculated.

(B) an Evaluation Method [1] Flexibility Evaluation Test

Figure 4A:
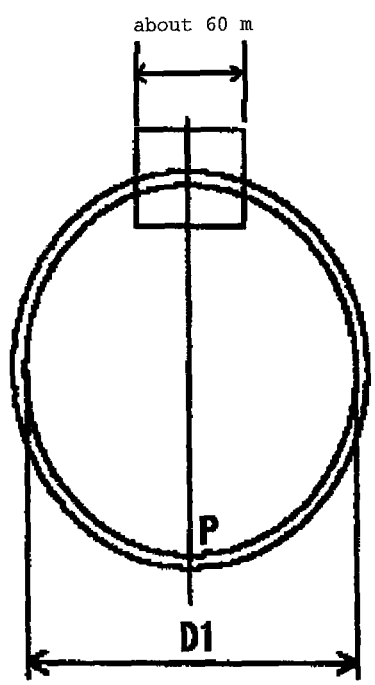
FIGS. 4(A) and 4(B) are diagrams which illustrate a flexibility evaluation test method performed on the composite cable in the first exemplary embodiment of the present disclosure.
Figure 4B:
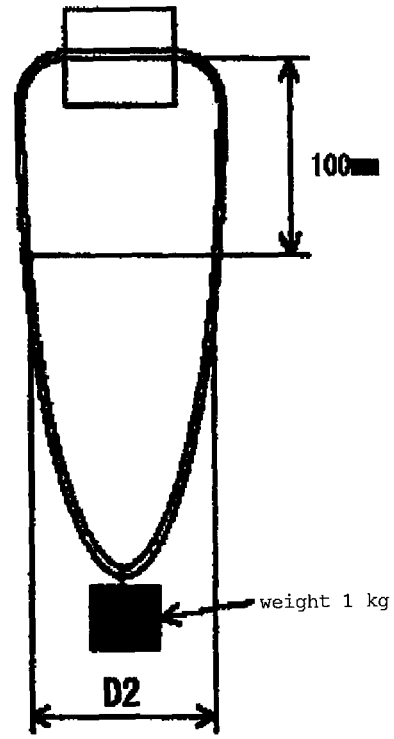

A method of a present evaluation test is illustrated in FIGS. 4(A) and 4(B). As illustrated in FIG. 4(A), when the entire cable is suspended in the hoop shape while having a clamp distance of 65 m in a clamp portion C, a maximum value for the inner diameter width of the hoop is measured as D1 (200±10 mm) and the inner diameter width of the hoop at the position 100 mm from the top edge of the hoop (measuring position is 100 mm from clamp portion) when the hoop is subjected to the load of 1 kg (weighting 1 kg) as illustrated in FIG. 4(B) is measured as D2, and then, a length (mm) of the condition D1−D2 is measured. By increasing the length of the condition D1−D2, the cable may be evaluated to have the high pliability and flexibility. Especially, it is emphasized whether the condition D1−D2>70 mm is satisfied or not.

[2] Lateral Pressure Performance Evaluation Test

Figure 5:
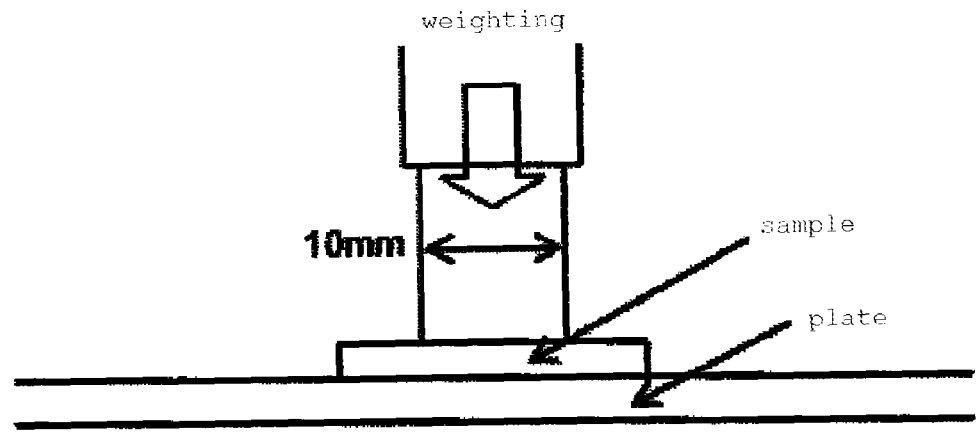
FIG. 5 is a diagram which illustrates a lateral pressure performance evaluation test method performed on the composite cable in the first exemplary embodiment of the present disclosure.

A method of a present evaluation test is illustrated in FIG. 5. As illustrated in FIG. 5, a weighting is measured and then evaluated when a sample of the cable having a length of 100 mm is placed on a plate, a width and a speed of the weighting are 100 mm and 5 mm/min, and the sample is pushed in by 30% of the inner diameter of the sample. By increasing the weighting, lateral pressure resistance performance becomes higher and the cable is evaluated to have the high deformation performance

[3] Resistance R Performance Evaluation Test

Figure 6:
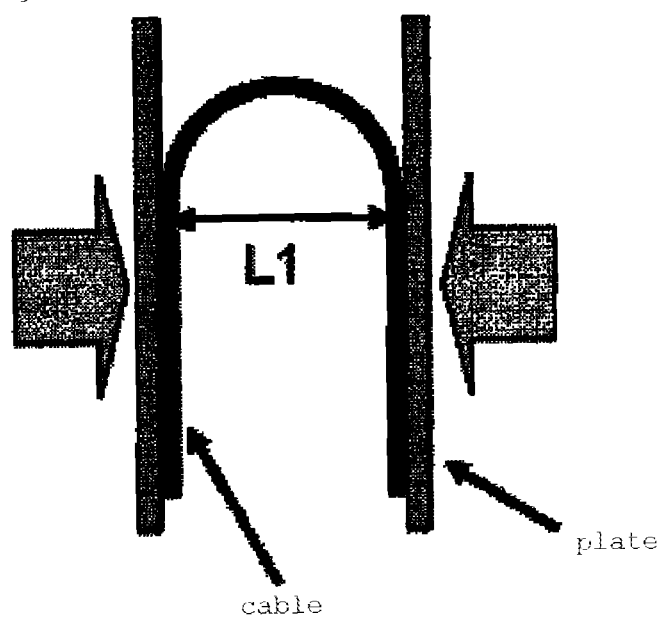
FIG. 6 is a diagram which illustrates a resistance R performance evaluation test method performed on the composite cable in the first exemplary embodiment of the present disclosure.

A method of a present evaluation test is illustrated in FIG. 6. As illustrated in FIG. 6, L1 (mm) is measured and then evaluated when a sample of the tube having a length of 200 mm is interposed between two sheets of plates, the sample is compressed between the plates, and buckling begins. By decreasing this L1 (mm), curvature at which the buckling begins becomes smaller, and therefore, the resistance R performance is high and the cable is evaluated to have the high deformation resistance performance. Simply, a minimum value (upper limit) of the L1 (mm) is 10 mm (C) Evaluation Result Evaluation results of the above-described three tests are disclosed in Table 2.

the FEP also withstand the lateral pressures 68.8 (N) and 280.0 (N) respectively, but it is evaluated that the flexibility is decreased although the lateral pressure resistance performance is good in the tube of the solid structure, which is identical to the typical example result.

Further, in the resistance R performance, in the samples (examples) 1 to 6 made from the ePTFE, the samples 2 to 6 withstand buckling to a minimum value 100 mm of the L1 (mm), and therefore, the high resistance R performance can be obtained. Further, the sample 1 also withstands buckling to 15 mm of the L1 (mm), and the good resistance R performance can be obtained. In this regard, in the samples (comparative examples) 7 and 8 made from the FEP, the sample (comparative example) 8 can withstand buckling to a minimum value 100 mm of the L1 (mm), and therefore, the high resistance R performance can be obtained whereas the sample (comparative example) 7 can withstand buckling only up to 30 mm of the L1 (mm), and therefore, the enough resistance R performance cannot be obtained. With this, even in the samples (comparative examples) 7 and 8 using the tube of the solid structure, it is derived that the enough

|  | 1 | 2 | 3 | 4 | 5 | 6 | 7 | 8 | 9 |
|---|---|---|---|---|---|---|---|---|---|
|  |  |  |  |  | Material |  |  |  |  |
|  |  |  | EPTFE |  |  |  | FEP |  | Cable |
| Size | Ø4.4-6.0 | Ø4.4-6.0 | Ø4.4-6.0 | Ø1.5-6.0 | Ø1.5-6.0 | Ø1.5-6.0 | Ø4.4-6.0 | Ø1.5-6.0 | — |
| Thickness | 0.8 T | 0.8 T | 0.8 T | 2.25 T | 2.25 T | 2.25 T | 0.8 T | 2.25 T | — |
| Width average of crevasse (μm) | 10.7 | 13.4 | 19.8 | 16.1 | 20.2 | 27.2 | 0 | 0 | — |
| (D-d)/D | 0.27 | 0.27 | 0.27 | 0.75 | 0.75 | 0.75 | — | — | — |
| Flexibility (mm) | 80 | 90 | 100 | 80 | 85 | 90 | 45 | 25 | 95 |
| Lateral pressure (N) | 73.0 | 48.6 | 31.9 | 72.0 | 61.2 | 37.1 | 68.8 | 280.0 | — |
| Deformation (mm) | 15 | 10 or less | 10 or less | 10 or less | 10 or less | 10 or less | 30 | 10 or less | — |
| Flexibility | ○ | ◎ | ◎ | ○ | ◎ | ◎ | x | x | ◎ |
| Lateral pressure | ◎ | ○ | Δ | ◎ | ○ | Δ | ◎ | ◎ | — |
| Deformation | ○ | ◎ | ◎ | ◎ | ◎ | ◎ | x | ◎ | — |

As disclosed in Table 2, in the flexibility evaluation test, all of the samples (examples) 1 to 6 using the tube made from the ePTFE satisfy a condition D1−D2>70 mm and therefore the good flexibility can be obtained, and particularly, the sample 2 satisfies a condition D1−D2>90 mm, the sample 3 satisfies a condition D1−D2>100 mm, the sample 5 satisfies a condition D1−D2>85 mm, and the sample 6 satisfies a condition D1−D2>90 mm, and therefore, the high flexibility can be obtained. In this regard, the samples (comparative example) 7 and 8 using the tube made from the FEP respectively satisfy only a condition D1−D2>45 mm and a condition D1−D2>25 mm, and therefore, it is not possible to obtain enough flexibility. Further, the composite cable (comparative example) 9 using the cable instead of the tube 2 satisfies a condition D1−D2>95 mm, and therefore, the entire composite cable can obtain the high flexibility.

Further, in the lateral pressure evaluation test, the sample 1 can withstand the lateral pressure of 73.0 (N) and the sample 4 can withstand the lateral pressure of 72.0 (N) in the samples (examples) 1 to 6 using the tube made from the ePTFE, and therefore, the high lateral pressure resistance performance can be obtained. In this regard, the samples (comparative examples) 7 and 8 using the tube made from resistance R performance is not obtained although such an enough thin thickness is provided like in the sample (comparative example) 7.

Figure 7:
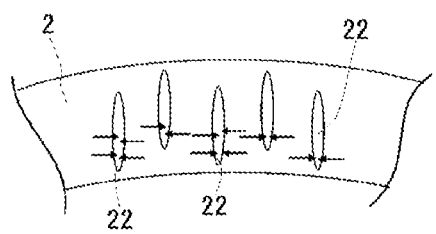
FIG. 7 is a diagram which discloses an action mechanism (mechanism) of improving flexibility by the porous structure.
Figure 8:
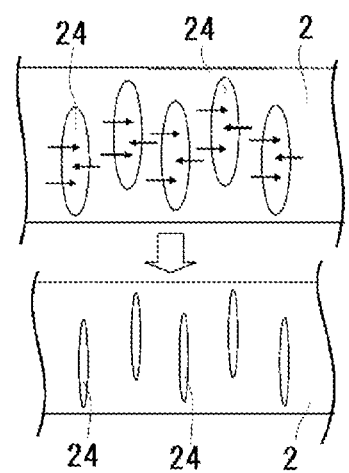
FIG. 8 is a diagram which discloses an action mechanism (mechanism) of improving lateral pressure resistance performance by the porous structure.
Figure 9:
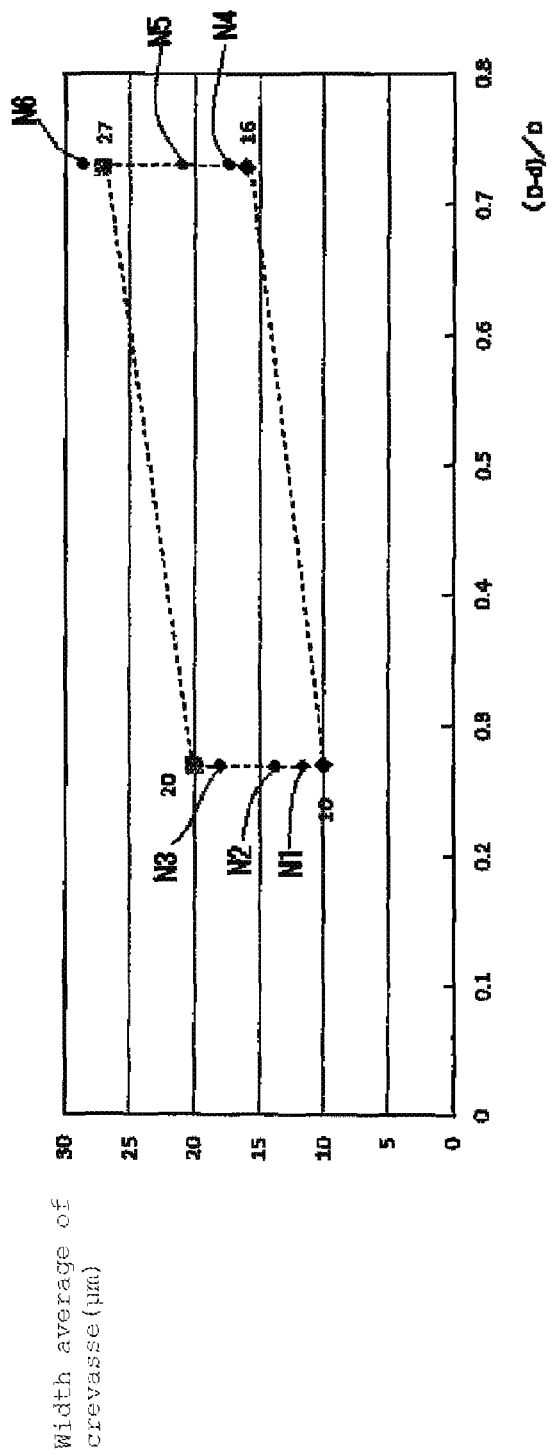
FIG. 9 is a graph which illustrates a preferred range of an average crevasse width in the porous structure.

Here, in the composite cable of the present disclosure, operation effects of the tube 2, which is made from the ePTFE and has the predetermined porous structure, will be described in association with the respective evaluation test results by referring to FIG. 7 to FIG. 9. FIG. 7 is a diagram which discloses an action mechanism (mechanism) of improving the flexibility by the porous structure, and FIG. 8 is a diagram which discloses an action mechanism (mechanism) of improving the lateral pressure resistance performance by the porous structure.

First, it is understood that the flexibility is deteriorated if the crevasse width becomes shorter, and the flexibility is improved if the crevasse width becomes longer. That is, at an interface of the cable, since the compression is performed on the inner side and then tension is generated on the outer side, when force is applied to the cable in a bending direction, though the action of the force between inner and outer sides is different (bending moment), in terms of flexibility, it is largely affected by compression particularly performed on the inner side in consideration of the flexibility. In the cable, which provides the tube having the solid structure, in the same way as the typical example or the samples (comparative examples) 7 and 8, reaction force to a compression energy of the tube itself directly acts. Meanwhile, in the composite cable of the present disclosure, that is, in the cable in which the tube 2 having the porous structure is provided as the same way as the samples (examples) 1 to 6, by increasing the crevasse width to form a gap corresponding the crevasse width on the tube, the compression energy is used to deform the crevasse 22 while the gap is being filled as illustrated in FIG. 7, so that the compression energy acted on the inner side of the tube is decreased. With this, by increasing the crevasse width, the flexibility is improved to enhance freedom of a degree for the compression of the tube.

Next, the lateral pressure is improved if the crevasse width becomes shorter, and the lateral pressure is deteriorated if the crevasse width becomes longer. That is, when the force is applied to the cable in a radial direction, repulsion from the pressure acts on the corresponding entire portion of the tube in the cable in which the tube having the solid structure is provided in the same way as the typical example or the samples (comparative examples) 7 and 8. With this, in the cable in which the tube of the porous structure is provided, as illustrated in FIG. 8, the portion of the node is eroded while the node 24 of the porous structure is displaced by the pressure, so that the pressure is buffered and the reaction force is decreased, in the same way of the composite cable in the present disclosure, that is, in the samples (examples) 1 to 6. For this reason, by increasing the aforementioned crevasse width, the reaction force is decreased. With the above grounds, characteristics of the lateral pressure are deteriorated by increasing the aforementioned crevasse width, and if the crevasse width becomes over a predetermined value corresponding to the thickness or the outer diameter of the tube, it is difficult to achieve both the flexibility and the lateral pressure. From this meaning, it is needed to generalize which region of a predetermined value is preferred for the aforementioned crevasse width.

Further, since the resistance R is deteriorated if the crevasse width becomes shorter and the resistance R is improved if the crevasse width becomes longer, the same point of view as the action mechanism of the flexibility may be applied to an action mechanism of resistance R test.

Further, in the typical example or the samples (comparative examples) 7 and 8 in which the tube having the solid structure is used, an impermissible range in resin deformation is determined on characteristic with respect to a predetermined amount or more of bending. With this, in the composite cable of the present disclosure, that is, in the samples (examples) 1 to 6 having the porous structure, with the deformation of the resin, the permissible amount is increased with the crevasse. Further, as the crevasse width is increased, the permissible amount tends to be increased.

In view of the above, it is started to generalize which range of the predetermined value is preferred for the aforementioned crevasse width. The result is illustrated in FIG. 9. FIG. 9 is a graph which illustrates a preferred range of the crevasse width. In the inventor's knowledge, if the outer diameter and the inner diameter of the tube are respectively defined as (D) and (d) as illustrated in FIG. 9, it is preferred that the condition (D−d)/D falls within the range of 0.27 to 0.75 and has the predetermined porous structure inside the region obtained by joining the following four points: the two points at which the crevasse width of the porous structure in the ePTFE has the minimum value of 10.0 μm and the maximum value of 20.0 μm when the ratio (D−d)/D is 0.27, and the two points at which the minimum value is 16.0 μm and the maximum value is 27.0 μm when the ratio (D−d)/D is 0.75.

As described above, since the tube is made from the ePTFE, the composite cable of the present exemplary embodiment has improved the flexibility and the pliability as compared to the typical composite cable which uses the tube made from only the polytetrafluoroethylene (PTFE) of the solid structure. Further, if the outer diameter and the inner diameter of the tube are respectively defined as (D) and (d), the condition (D−d)/D falls within the range of 0.27 to 0.75 and has the predetermined porous structure inside the region obtained by joining the following four points: the two points at which the average crevasse width of the porous structure in the ePTFE has the minimum value of 10.0 μm and the maximum value of 20.0 μm when the ratio (D−d)/D is 0.27, and the two points at which the minimum value is 16.0 μm and the maximum value is 27.0 μm when the ratio (D−d)/D is 0.75, so that the fine deformation resistance performance can be obtained. Further, in the composite cable, when the composite cable is suspended in the hoop shape with the entire composite cable as the cable to be tested, if the maximum value for the inner diameter width of the hoop is measured as D1 and the inner diameter width of the hoop at the position 100 mm from the top edge of the hoop when the hoop is subjected to the load of 1 kg is measured as D2, the condition D1−D2>70 mm is satisfied, and therefore, the flexibility and the pliability over the entire composite cable can be secured.

Further, the plurality of signal lines are formed of signal lines which respectively include the inner conductor and the outer conductor which is disposed around the inner conductor, and each outer diameter of the inner conductor is desirably 0.123 mm With this configuration, the pliability and the flexibility over the entire composite cable can be further improved. Furthermore, in the inventor's knowledge, the hardness of the entire composite cable depends the hardness of the inner conductor of the signal line around the tube as well as the hardness of the tube, and the entire composite cable becomes harder by increasing the outer diameter of the inner conductor, and therefore, if the outer diameter of the inner conductor becomes 0.123 mm or less, the pliability and the flexibility over the entire composite cable can be further improved.

Figure 10:
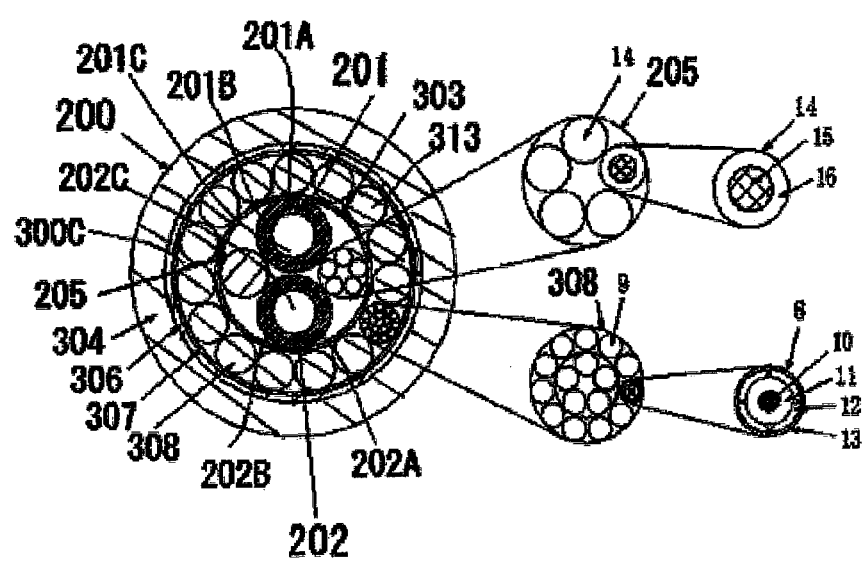
FIG. 10 is a partially enlarged cross-sectional view of a composite cable in the second exemplary embodiment of the present disclosure.

FIG. 10 is a partially enlarged cross section of a composite cable in the second exemplary embodiment of the present disclosure. A composite cable 200 in the second exemplary embodiment includes two tubes 201 and 202, for example, in which fluid for cooling reciprocates, and therefore, optical fibers are not inserted into the two tubes 201 and 202 and the two tubes 201 and 202 have hollows. Further, in the composite cable of the second exemplary embodiment, the two tubes 201 and 202 have two-layer structures having first tube layers 201A and 202A, which are made from the ePTFE and have a predetermined porous structure as the same as the tube in the first exemplary embodiment, and second tube layers 201B and 202B, which have a different solid structure from the predetermined porous structure on inner sides of the first tube layers. With this, since the respective tubes have the second tube layers 201B and 202B of the solid structure on inner sides, liquid which flows in the tube 201 and 202 may not leak outside, so that when the liquid for cooling flows into the tubes 201 and 202, it is safely used and high reliability can be obtained.

That is, the composite cable in the second exemplary embodiment of the present disclosure has the tubes 201 and 202, which are disposed adjacent to a center portion of a cross section of the composite cable 200, and cables 205, which are formed of simple line units 5 disposed on both side of the tubes 201 and 202, as illustrated in FIG. 10. The cables 205 are formed of five cores of the simple line units 14, and each simple line unit 14 has an inner conductor 15 and an insulator 16 around the inner conductor.

The respective tubes 201 and 202 have cavities 201C and 202C, such that the fluid for cooling reciprocates and is circulated within the cavities 201C and 202C. On outer circumferential surfaces of the tubes 201 and 202 and the cables 205, a tape 303 is wound, and an outer side of the tape 303 is referred to as a cable accommodation portion 300C. In the cable accommodation portion 300C, a plurality of cable units 308 and interpositions 313 are disposed throughout an outer circumference of the tape 303, and the cable units 308 and the interpositions 313 may be twisted each other. Outer sides of the twisted cable units 308 or the like are pressed by a press winding tape 307, an outer side of the press winding tape 307 is shielded by a collective shield layer 306, and a cable sheath 304, which is an outermost layer, is disposed on an outer side of the collective shield layer 304. Further, the respective cable units 307 are the same cable units 7 in the first exemplary embodiment.

Further, the second tube layers 201B and 202B on the inner sides of the two tubes 201 and 202 have desirably the solid structure, for example, the second tube layers 201B and 202B may be formed of fluorine resin in which an end group is fluorinated, and fluorinated (stabilized) tetrafluoro-ethylene-perfluoroalkyl vinyl ether copolymer (hereinafter, referred to as "PFA") having an end group of $CF_3$ may be used as the fluorine resin. With this, the tubes 201 and 202 may be tubes of a multilayer structure which include at least of the first tube layers 201A and 202A of the predetermined porous structure and the second tube layers 201B and 202B of the different solid structure from the predetermined porous structure. With this configuration, the liquid of the like, which flows within the tubes 201 and 202, may not leak outside by the second tube layers 201B and 202B of the solid structure, so that it can be safely used and quality stability and reliability can be secured even when the liquid for cooling or the like flows within the tube.

Further, the one tube is included in the center of the composite cable in the above-described first exemplary embodiment and the two tubes are included in the second exemplary embodiment, but three tubes or more may be included. Furthermore, the tube has a single layer structure in the above-described first exemplary embodiment, and the tube has the two-layer structure in the second exemplary embodiment, but the tube may have a multilayer structure having three layers or more layers. In aspects of this multilayer structure, either the inner layer or the outer layer may have the porous structure and the other one may have the solid structure, or a multilayer sandwich structure (center, either inner side member or outer side member with porous structure, the other with solid structure). Meanwhile, even when the tube of the multilayer structure is adopted, thicknesses of other layers than the porous structure are adjusted to be in a range to satisfy the above-described condition D1–D2>70 mm with respect to the flexibility over the entire composite cable. Moreover, the tube may be formed by twisting the plurality of tubes each other.

INDUSTRIAL APPLICABILITY

The present disclosure may be applicable to composite cables for all purposes as well as the composite cable, which connect the medical device and the terminal end.

DESCRIPTION OF REFERENCE NUMBERS 2, 201, 202 tube 1, 200 composite cable 111 test cable

What is claimed is:
1. A composite cable comprising a tube and a plurality of cables inside of a sheath,
   wherein, when the composite cable is suspended in a hoop shape with an entire composite cable as a cable to be tested, if a maximum value for an inner diameter width of the hoop is measured as D1 and the inner diameter width of the hoop at a position apart from a top edge of the hoop by 100 mm when the hoop is subjected to a load of 1 kg is measured as D2, a condition D1–D2>70 mm is satisfied,
   the tube partially or entirely comprises a layer made from porous polytetrafluoroethylene (ePTFE), and
   if an outer diameter and an inner diameter of the layer of the tube are respectively defined as (D) and (d), a condition (D–d)/D falls within a range of 0.27 to 0.75, and has a predetermined porous structure inside a region obtained by joining following four points: two points at which an average crevasse width of the porous structure in said ePTFE has a minimum value of 10.0 μm and a maximum value of 20.0 μm when a ratio (D–d)/D is 0.27, and two points at which the minimum value is 16.0 μm and the maximum value is 27.0 μm when the ratio (D–d)/D is 0.75.

* * * * *